United States Patent [19]

Kushida et al.

[11] 4,028,642
[45] June 7, 1977

[54] CIRCUIT FOR CONVERTING A TEMPERATURE DEPENDENT INPUT SIGNAL TO A TEMPERATURE INDEPENDENT OUTPUT SIGNAL

[75] Inventors: Toshimoto Kushida, Dearborn; Eleftherios M. Logothetis, Birmingham, both of Mich.

[73] Assignee: Ford Motor Company, Dearborn, Mich.

[22] Filed: Oct. 3, 1975

[21] Appl. No.: 619,344

Related U.S. Application Data

[62] Division of Ser. No. 494,269, Aug. 2, 1974, Pat. No. 3,915,135, which is a division of Ser. No. 375,993, July 2, 1973, Pat. No. 3,868,846.

[52] U.S. Cl. .................. 323/75 B; 323/75 H; 324/98
[51] Int. Cl.² ........................................ G01R 17/02
[58] Field of Search .................. 323/16, 19, 40, 68, 323/69, 75 B, 75 H, 75 N; 324/71 SN, 98, 105

[56] References Cited

UNITED STATES PATENTS

| | | | |
|---|---|---|---|
| 2,278,633 | 4/1942 | Bagnall | 323/75 N |
| 2,947,935 | 8/1960 | Sepmeyer | 323/75 N |
| 3,278,834 | 10/1966 | Perino | 324/105 X |

*Primary Examiner*—A. D. Pellinen
*Attorney, Agent, or Firm*—Robert A. Benziger; Keith L. Zerschling

[57] ABSTRACT

A bridge circuit for combination with a variable resistance sensor whose resistance may vary as a function of a sensed variable and also as a function of a parasitic variable such as, for example, temperature. The bridge circuit includes at least one variable resistance which varies as a function of the parasitic parameter and is relatively insensitive to the sensed parameter. The bridge circuit comprises a first leg incorporating the sensor resistor having a tap junction whose voltage varies as a function of the sensed parameter and of the parasitic parameter, a second leg including the parasitic parameter responsive resistance and having a voltage tap whose voltage varies only as a function of the parasitic parameter and a third leg interconnecting the first and second leg voltage taps and having a signal tap whose voltage varies only as a function of the sensed parameter. In a preferred embodiment, a resistance type exhaust gas sensor whose resistance varies as a function of the partial pressure of oxygen in the exhaust system of an internal combustion engine and also as a function of the temperature of the environment of the exhaust system is compensated by the circuit of the present invention to remove temperature dependency effects.

5 Claims, 3 Drawing Figures

CIRCUIT FOR CONVERTING A TEMPERATURE DEPENDENT INPUT SIGNAL TO A TEMPERATURE INDEPENDENT OUTPUT SIGNAL

This is a division of application Ser. No. 494,269, filed Aug. 2, 1974, now U.S. Pat. No. 3,915,135, which is a division of Ser. No. 375,993, filed July 2, 1973, now U.S. Pat. No. 3,868,846.

BACKGROUND OF THE INVENTION

1. Field of the Invention

The present invention is related to the field of bridge circuits and more particularly, to that portion of the field which is concerned with bridge circuits for eliminating the effect of a variable on an output signal. More particularly, the present invention is related to a bridge circuit which may be used in conjunction with a resistive sensor whose resistance varies as a function of two potentially interrelated parameters and which will render an output signal which varies only in response to a selected one of the parameters. The present invention is also related to the field of exhaust gas responsive engine control systems wherein a signal derived from an exhaust gas sensor is used to control the provision of air/fuel mixture to the engine.

2. Description of the Prior Art

The prior art teaches that an exhaust gas sensor may be positioned in the exhaust system of an internal combustion engine to monitor the combustion process and that the output signal from this sensor may be used to control the combustion process to maintain combustion at an optimum level whereat the deleterious exhaust emission products may be at an optimum value. For example, such a sensor may monitor the pressure of oxygen within the exhaust system as a measure of the quality of the combustion process and may control that combustion process by modulating, for example, the ratio of the air/fuel mixture to maintain that mixture at a selected ratio. This is of importance in the automotive industry which is being compelled to rely upon catalytic reactors or converters to treat the exhaust gases to arrive at mandated minimum values of hydrocarbons (HC), carbon monoxide (CO) and oxides of nitrogen ($NO_x$). The most efficient and reliable catalytic converters require that the exhaust gas which enters the converter be the product of a combustion process which has occurred within a very narrow range of air/fuel ratios centered about a ratio which yields a particular exhaust gas chemistry. This ratio may be the stoichiometric ratio. The margin for error in the air/fuel ratio is very slight and exceeding this margin may result in catastrophic failure of the catalytic reactor or in grossly inefficient operation of the catalytic converter.

Extensive work is being undertaken in the area of the exhaust gas sensors and several sensors are known which, when inserted within the exhaust system, will generate a first relatively high level of signal when the combustion process occurs on one side of the stoichiometric ratio and a second relatively low level of signal when the combustion process occurs on the other side of the stoichiometric ratio. For example, the output signal may be high for mixtures rich in fuel content and may be low for mixtures which are lean in fuel content. The transition from the high level of signal to the low level of signal occurs as a virtual step at the stoichiometric ratio. Careful analysis of this output signal, particularly around the stoichiometric ratio, has demonstrated that the signal change is not in fact a step function but is a monotonically changing function from about the stoichiometric ratio minus two tenths of an air/fuel ratio to about the stoichiometric ratio plus two tenths of an air/fuel ratio.

For any given engine design and catalyst used therewith, the optimum engine performance, considering efficiency, economy and emissions, may be at an air/fuel mixture ratio which deviates from the stoichiometric ratio. For example, the engine design may inherently result in low output of one emissions component for example $NO_2$ so that the engine could be set to run slightly less where more $NO_x$ may be generated, which is within the capability of the catalyst to convert, while improving economy. Thus determining the desired ratio requires taking into account the engine performance and the catalyst capabilities. At present, the preferable catalyst and most engines require an air/fuel mixture ratio which is slightly rich.

Control systems which respond to the output signal from such a sensor have been proposed to modulate the air/fuel ratio of the air/fuel mixture entering the engine. According to one proposal, a conventional carburetor would provide an air/fuel mixture having a grossly controlled air/fuel ratio less than stoichiometric and an auxiliary device would be provided, such as, for example a continuous flow fuel nozzle which would add additional quantities of fuel to render the total air/fuel mixture provided to the engine at the desired ratio. This continuous flow auxiliary nozzle may be for example a solenoid controlled needle valve positioned within a metering orifice. The quantity of fuel provided thereby would be controlled by the output signal of a system sensing the exhaust gases and variably energizing the solenoid to position the needle valve within the metering orifice to thereby add to or subtract from the quantity of fuel in the mixture being provided to the engine. According to another proposal, the system would control the position of an air valve whereby the quantity of air being admitted to the intake of the carburetor would be controlled to render the overall air/fuel mixture at the desired ratio. Still another proposal has involved the modulation of the scheduling of a scheduled electronic fuel injection system to continuously tailor the scheduling so that the quantity of fuel being provided to the engine would be exactly that necessary to provide a stoichiometric mixture for the combustion chambers of the engine.

Each of these systems relies upon establishing a mean value of sensor signal which would represent, for example, the stoichiometric ratio and then establishing error limits which would be within the range of acceptable combustion products for the associated catalytic reactor. For example, in a catalytic reactor that operates efficiently at 99 to 101% of the stoichiometric air/fuel ratio, the limits established by the control system could be at 99.5 and 100.5% of the stoichiometric air/fuel ratio so that when the output signal of the exhaust sensor reaches these limits, the device controlled by the system (e.g., the continuous flow orifice, the air valve or the scheduling for an electronic fuel injection system) would be actuated to increase or decrease the air/fuel ratio to cause the sensed exhaust gas signal to move away from the limit which it had approached toward the center value. This results in a system which has very tight tolerances and very small margin for error. This is, nevertheless, well within the capabilities of electronics to meet.

Copending commonly assigned patent application Ser. No. 198,515, now abandoned, "Air Fuel Ratio Sensing System" by H. L. Stadler et al. discloses an exhaust gas sensor of the resistive type which has been found to be most advantageous in examining exhaust gases for determining the air/fuel ratio of the combustion mixture. The sensor disclosed therein operates most efficiently, at least in an internal combustion engine environment, at temperatures within the range of from about 600° C to about 900° C. Such a temperature range presents wide latitude in the placement of such a sensor within the exhaust system and also permits efficient sensor operation under all, or virtually all, conceivable engine operating conditions. Extensive testing with this type of sensor under all engine operating conditions has pointed out an area of significant difficulty with this type of sensor which has been determined to reside in the fact that the output signal of such a sensor includes a temperature dependent or parasitic component. This temperature dependent component can combine with (either add to or subtract from) the exhaust gas indicative signal component to skew the air/fuel ratio away from the stoichiometric ratio and, under extreme conditions, can result in air/fuel ratios being commanded which will exceed the limits which the associated catalytic converter or converters may efficiently accept. Maintaining the sensor at a precisely controlled temperature within its operating range would be one way of eliminating this temperature dependency problem. However, the exhaust system of an internal combustion engine is a highly dynamic environment and maintaining a constant temperature would be difficult and expensive and would require the provision of both heating and cooling mechanisms within the sensor, or alternatively placement at a relatively lower temperature environment and constant heating of the sensor. This would also entail complex sensing and control mechanism to ensure that the temperature of the sensor is maintained at a fixed and controlled level. This would greatly increase the cost of the sensor and would also represent a potential cause of failure since placement in a cooler region coupled with lack of heating as for example with a broken heater wire would cause the sensor to operate at a temperature environment at which it is most inefficient, for example below 600° C. It is also an object of the present invention to provide an electrical system for temperature compensation of a sensor, which system is inexpensive and which is more reliable because it does not include failure-prone devices such as power transistors operated under marginal condition. It is also an object of the present invention to provide a means for eliminating temperature dependency which means may be efficiently incorporated within the overall control system.

According to the above noted copending commonly assigned patent application Ser. No. 198,515, now abandoned, the exhaust gas sensor may be advantageously constructed of a disc or pellet of ceramic titania. Such a material demonstrates a temperature dependent resistivity which is an exponential function of the absolute temperature. It is therefore a further object of the present invention to provide a circuit which may be combined with a variable resistance, which may be for example titania ceramic material, to provide an output signal which is temperature independent at least over a selected temperature range. In order to accomplish the last-mentioned objective, it is a further object of the present invention to provide a circuit which will firstly define a region of temperature dependency of the resistivity of the titania sensor in which the temperature dependency is a substantially linear function and which will combine the signal derived therefrom with a signal which demonstrates an opposite linearity so that the resultant signal becomes temperature independent.

SUMMARY OF THE PRESENT INVENTION

The present invention provides an electrical circuit which may include, as a portion of a bridge network, the variable resistance titania sensor and which further combines the sensor with a variable resistance which is variable as a function of temperature further provides trim resistances for each of these variable resistances so that the voltage drop across selected pairs of these resistances, as a function of temperature, will demonstrate linear temperature dependencies of opposite slope at least over a selected temperature range.

A further voltage divider interconnects these voltages and is provided with resistances whose ratio is substantially the same as the ratio of the slopes of the two temperature dependent voltage signals. This provides at a selected terminal which may be designated the output terminal a temperature compensated signal whose value or magnitude is temperature independent.

In the preferred embodiment of the present invention, a titania sensor is connected electrically in series with a first trim resistance and a platinum heater wire is connected electrically in series with a second trim resistance. Since titania demonstrates a negative slope temperature dependency and platinum resistance wire demonstrates a positive slope temperature dependency, the titania and the platinum wire are provided with an electrically common terminal and the junctions between each of the variable resistances and their trim resistors are interconnected by a voltage divider having a central terminal. The ratio of the magnitudes of the resistances in the voltage divider is arranged to be substantially equal to the ratio of the magnitudes of the slopes of the temperature dependent curves over the selected temperature region. The circuit further provides for a second voltage divider connected in parallel with the variable resistances and fixed trim resistances so that the central or tap point thereof has a voltage value which is calculated to be equal to the voltage value derived from the center tap of the first voltage divider when the exhaust gas sensor is sensing a condition of the ratio of the combustion mixture being at the desired, for example the stoichiometric, value.

An operational amplifier is connected to these last mentioned terminals so that the output signal thereof will be of a magnitude representative of the degree of error between the measured air/fuel ratio and the optimum or stoichiometric air/fuel ratio while the electrical polarity of this signal with respect to the established reference value will be of an electrical sense so that it may be directly applied to an air/fuel ratio modulator to cause corrective action at the modulator.

DETAILED DESCRIPTION OF THE PREFERRED EMBODIMENT

Figure 1:
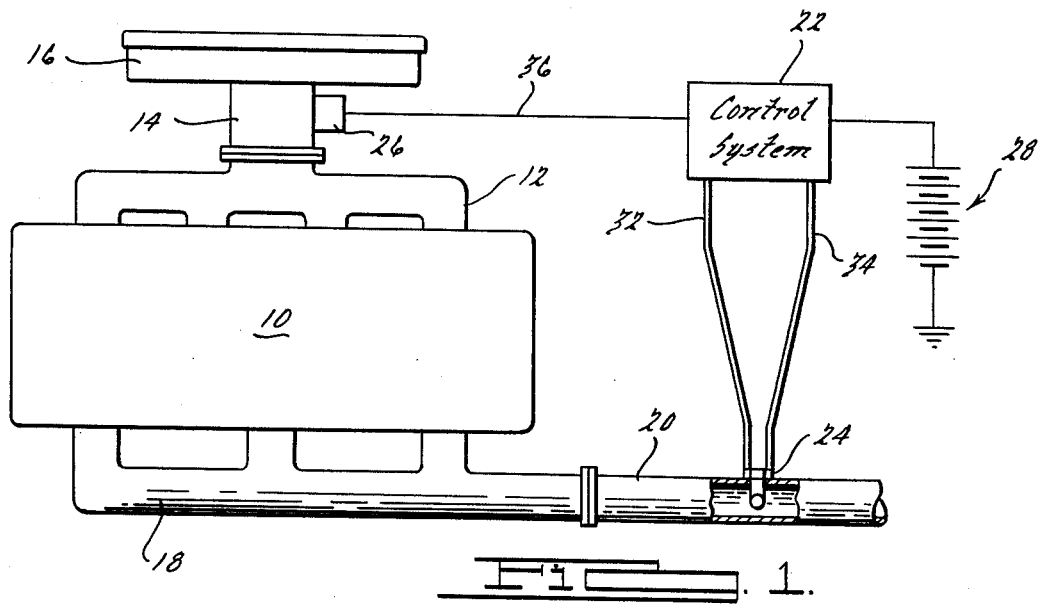
FIG. 1 illustrates schematically an internal combustion engine having an air/fuel ratio control system responsive to a sensed exhaust gas parameter.

Referring now to the drawing wherein like numbers designate like components in the various views, FIG. 1 illustrates an internal combustion engine and associated air/fuel ratio control system responsive to an exhaust gas parameter. An internal combustion engine 10 is provided with an inlet or intake manifold 12 which has mounted thereon a fuel metering device 14, which may be for example a carburetor, and air cleaner 16. Internal combustion engine 10 is also provided with exhaust manifold 18 which communicates the combustion by-products from the combustion chambers of the engine 10 through an exhaust pipe 20 to the atmosphere.

FIG. 1 also illustrates a control system 22 which is responsive to an exhaust gas sensor, shown situated in the exhaust pipe 20 but which may also be located in the exhaust manifold 18, operative to control air/fuel ratio modulator 26. Control system 22 is energized by battery 28 which may be for example the normally provided vehicle battery. Control system 22 communicates with exhaust gas sensor 24 through two pairs of electrical leads 32 and 34 and communicates with air/fuel ratio modulator 26 over lead 36.

Air/fuel ratio modulator 26 may be for example an electrical scheduling control arranged to variably control fuel scheduling in an electronic fuel injection system or a continuous flow fuel delivery device arranged to add supplementary amounts of fuel to that normally provided by fuel metering device 14 and may have for example a solenoid controlled variably positioned needle valve and metering orifice combination. Alternatively, modulator 26 may be arranged to control a variable flow fuel orifice within fuel metering device 14 and arranged to increase or decrease the size of the orifice about some median position. Modulator 26 may also provide for variably positioning an air valve within manifold 12 to control the flow of air to the engine 10. This combination of carburetor 14 and air/fuel modulator 26 is intended to be merely illustrative of the many different forms of air/fuel ratio controls known.

Figure 2:
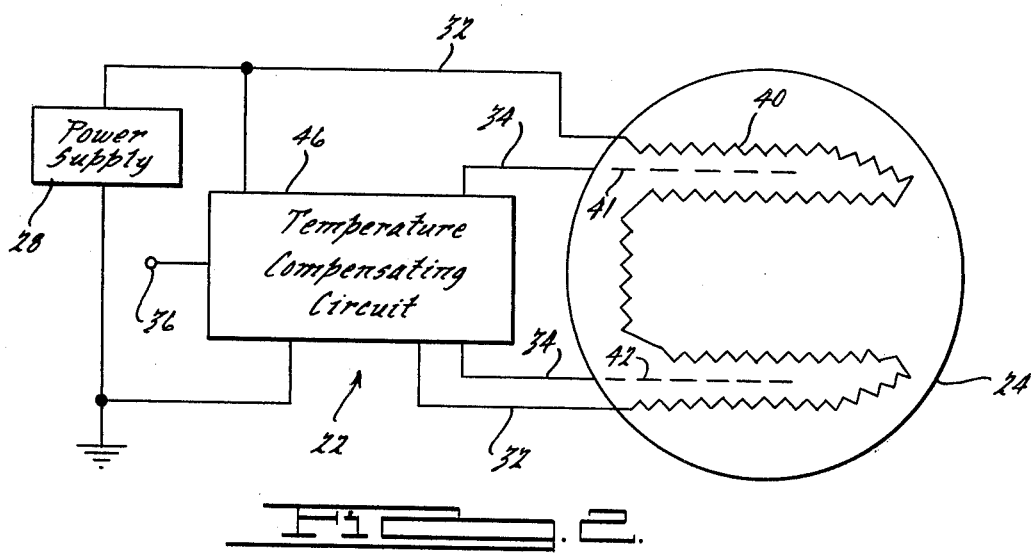
FIG. 2 illustrates an electrical schematic block diagram for the control system of FIG. 1.

Referring now to FIG. 2, the control system 22 and its relationship with the exhaust gas sensor 24 are further illustrated in electrical schematic view. Exhaust gas sensor 24 is comprised of a generally circular pellet of titania ceramic material and includes embedded therein an electrical heater wire 40 and a pair of resistance measuring electrodes 41, 42. The construction and operation of this device are more fully described in the above noted copending commonly assigned patent application Ser. No. 198,515, now abandoned.

Modulator control system 22 is comprised of the temperature compensating circuit 46 of the present invention. Circuit 46 communicates with the titania sensor leads 41, 42 over conductors 34 and also communicates with the heater wire 40 over second conductor 32 and provides the output signal to control the air/fuel ratio modulator 26 of FIG. 1 over conductor 36.

Figure 3:
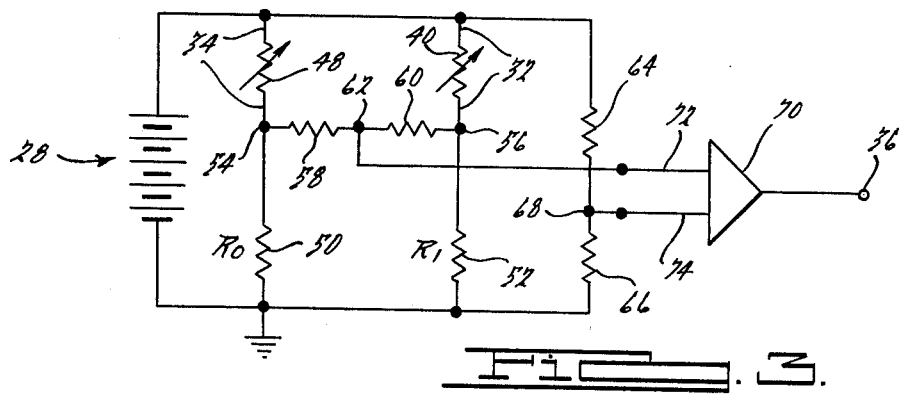
FIG. 3 illustrate the electrical compensation circuit of the present invention.

Referring now to FIG. 3, the temperature compensating circuit 46 of the present invention is illustrated in an electrical diagram which includes the variable resistance 48 representative of the resistance of the titania between the electrodes 41, 42 and also the variable resistance 40 representative of the heater element 40.

Trim resistance $R_0$, identified by the numeral 50, is arranged to be electrically in series with the variable resistance 48 of the titania sensor and trim resistance $R_1$, identified by the numeral 52, is arranged to be electrically in series with heater element 40. These two series-connected pairs of resistances are arranged to be in parallel across the voltage source here identified as battery 28.

Sensor resistance 48 and trim resistance 50 are arranged to provide a terminal 54 intermediate these two resistances while heater resistance 40 and trim resistance 52 have been arranged to provide a terminal 56 therebetween. Terminals or junctions 54, 56 are interconnected by a voltage divider network comprised of series resistances 58 and 60. Resistance 58 is connected to junction 54 and resistance 60 is connected to junction 56 so as to provide a junction 62 therebetween. This junction 62 comprises the output junction for the bridge network thus described. A further voltage divider network comprised of series-connected resistances 64, 66 energized by the voltage source identified herein as battery 28, is arranged to provide a reference voltage at a junction 68 intermediate the resistances 64,66. Output junction 62 and reference junction 68 are communicated to an operational amplifier 70. This device may be for example a $\mu$741 operational amplifier which is available from a large number of sources under the identifying number. The output of operational amplifier 70 may be directly communicated to conductor 36 so as to provide the control current flow for the air/fuel modulator 26 of FIG. 1. In the circuit thus described, the variable resistance 48 demonstrates a negative temperature coefficient. That is, as the temperature of the environment of resistance 48 (i.e., the titania material) increases, the resistance value decreases so that the voltage drop across this resistance also decreases. This results, in the illustrated embodiment, in the voltage value at junction 54 increasing relative to ground with increases in temperature of the environment of the titania sensor material. Conversely, heater element 40 which may be for example a platinum heater wire demonstrates a positive temperature coefficient. That is, as the temperature of its environment increases, the resistance of the element also increases so that the voltage appearing at the junction 56 will decrease, relative to ground, as the temperature of the environment of the heater element 40 increases. In this context, "increase relative to ground" is intended to mean that the voltage value becomes electrically more positive or electrically more negative than the ground value depending upon the electrical polarity of the voltage supply connections while "decrease relative to ground" means that the voltage value becomes electrically less positive or electrically less negative. By locating the heater element 40 physically surrounding the titania resistance sensor leads 41, 42 of FIG. 2, the environmental temperature of each element will be virtually identical.

Since the resistance of the titania material is an exponential function of temperature over its entire operating range, the resistance value of the resistor $R_o$ is selected so that the temperature dependency of the resistance value of the titania sensor demonstrates a substantially linear characteristic over the temperature range of interest. The value of $R_o$ can be determined by selecting a value $R_o$ with respect to the resistance of the titania material wherein the second derivative of the expression for the voltage at junction 54 with respect to temperature is zero at the midpoint of the temperature range of operation of the titania sensor material, for example at 700° C. This value is expressed by $$R_o = R_s \, \epsilon_{/kT_o} \frac{\left(\frac{\epsilon}{kT_o} - 2\right)}{\left(\frac{\epsilon}{kT_o} + 2\right)} \quad (1)$$

where $R_s$ is a measured sensor constant, $\epsilon$ is the activation energy of the sensor material, $T_o$ is the selected temperature and $k$ is the Boltzman's constant. A typical value for $R_o$ would be 1.5 kohm. $R_o$ may also be selected to be equal to the resistance of resistance 48 at the midpoint of the temperature range of operation.

Since the resistance value of the platinum heater element 40 increases linearly with the temperature, the voltage at junction 56 may be given by the expression $$V_{56} = V_{28} \frac{R_{52}}{R_{52} + R_{40}} \quad (2)$$

where $R_{40}$ is given by the expression $$R_{40} = RTK + \text{CONSTANT} \quad (3)$$

where $T$ is the temperature in °K and $K$ is the temperature coefficient of the heater element 40. The numerical value of resistance 52 may be selected to place the value of the voltage at junction 56 in a convenient range. Typically this may be a resistance of 4 ohms. This value may also be selected to equal the value of resistance 40 at the midpoint of the temperature range of operation.

In order to eliminate the temperature dependency, the ratio of the resistance 58 to the resistance 60 should be selected so as to satisfy the following equation:

$$\frac{R_{58}}{R_{60}} = -\frac{-\frac{dV_{54}}{dT}}{\frac{dV_{56}}{dT}} \quad (4)$$

that is, the ratio of resistance 58 to resistance 60 should equal the negative of the ratio of slopes of the voltage/temperature curves at the associated junctions. The magnitude of these resistances should be selected to be sufficiently high to prevent appreciable amounts of current flow therethrough. For example, values of from about 10 to about 100 kohm are preferable.

It will be apparent to the man of skill in this art that certain modifications and deviations may be made in the practice of the instant invention. For example, a substitution of a negative temperature coefficient device for the positive temperature coefficient device illustrated may be made wherein that device is located in the circuit of FIG. 3 in the position occupied by resistor $R_1$ and a fixed resistance may be then inserted in the position occupied by variable resistance 40. Other modifications and changes may be made in the bridge circuit of the present invention and such are contemplated within the scope of the instant invention.

By providing the series-connected sensor resistance 48 and trim resistance 50 in parallel with series-connected heater resistance 40 and trim resistance 52 and the voltage divider reference generating network of resistances 64, 66 all energized by the same source, the circuit of the present invention is rendered insensitive to fluctuations in the supply voltage since these fluctuations will be self-compensating with regard to the signals appearing at the two inputs 72, 74 of the operational amplifier 70. The inputs 72, 74 have not been identified with polarity indication in view of the fact that the reference junction may be connected to either polarity input depending upon the polarity of the output signal desired to drive the air/fuel ratio modulator 26 in respect to the correction desired.

We claim:

1. A bridge circuit, for use in conjunction with a variable resistor whose resistance varies predictably in response to a sensed parameter and which varies by a factor of $K_1$ in response to a parasitic parameter, to generate an output signal which is independent of the parasitic parameter comprising:
   a voltage source connected to the variable resistor;
   a first resistance connected in series relationship with the variable resistor and said source operative to provide a first electrical circuit;
   a first voltage divider connected to said source in parallel with said first circuit, said first voltage divider having at least one fixed resistance connected in series with at least one variable resistance;
   said at least one variable resistance selected to be variable only in response to the parasitic parameters and arranged to provide a voltage at the junction of the at least one fixed resistance and the at least one variable resistance which varies by a factor of $K_2$ in response to the parasitic parameter, $K_2$ being inversely related to the voltage variation demonstrated at the junction of the variable resistor and said first resistance in the presence of the parasitic parameter; and
   second voltage divider means comprising second and third fixed resistances connected in series to form a signal terminal therebetween, said second fixed resistance also connected to the junction of the variable resistor with said first resistance and said third fixed resistance connected to the junction of said at least one variable resistance with the at least one fixed resistance.

2. The bridge circuit of claim 1 wherein the ratio of the resistance value of the second fixed resistance to the resistance value of the third fixed resistance is substantially equal to the ratio of the magnitude of $K_1$ to the magnitude of $K_2$.

3. The circuit of claim 2 including further:
   a third voltage divider means having an intermediate reference terminal forming a current flow path electrically in parallel with said first voltage divider operative to generate a reference voltage signal at said reference terminal; and
   amplifier means having a pair of input terminals, each one of which is electrically connected to one of the signal and reference terminals, operative to produce an output signal having a magnitude and electrical sense relative to the voltage signal at the reference terminal indicative of the difference between the reference terminal voltage and the signal terminal voltage.

4. The circuit of claim 3 wherein said first resistance is selected to have a resistance value substantially equal to the resistance value of the variable resistor at a selected condition of the parasitic parameter.

5. The circuit of claim 4 wherein said fixed resistance is selected to have a resistance value substantially equal to the resistance value of said parasitic parameter responsive variable resistance at a selected condition of the parasitic parameter.

* * * * *